United States Patent [19]

Debras et al.

[11] Patent Number: 4,830,735
[45] Date of Patent: May 16, 1989

[54] PROCESS FOR REMOVING CARBONYL-SULFIDE FROM LIQUID HYDROCARBON FEEDSTOCKS

[75] Inventors: Guy L. G. Debras, Belgrade; Georges E. M. J. De Clippeleir, Sint Pieters Leeuw; Raymond M. Cahen, Brussels, all of Belgium

[73] Assignee: Labofina, S.A., Brussels, Belgium

[21] Appl. No.: 103,239

[22] Filed: Sep. 30, 1987

Related U.S. Application Data

[63] Continuation-in-part of Ser. No. 753,211, Jul. 9, 1985, abandoned.

[30] Foreign Application Priority Data

Dec. 19, 1986 [BE] Belgium ................................ 217559

[51] Int. Cl.$^4$ .......................... C10G 29/16; C07C 4/12
[52] U.S. Cl. ................................ 208/244; 208/208 R; 208/299; 585/855; 585/850; 423/244
[58] Field of Search ................... 208/299, 208 R, 244, 208/247, 310 R; 585/820, 823, 826, 829, 824, 850, 855; 423/244 R

[56] References Cited

U.S. PATENT DOCUMENTS

| | | | |
|---|---|---|---|
| 2,772,208 | 11/1956 | Ferm | 585/824 X |
| 2,951,034 | 8/1966 | Stuart | 585/850 |
| 3,058,800 | 10/1962 | Frevel et al. | 585/824 |
| 3,864,412 | 2/1975 | Murphy | 585/824 |
| 3,998,902 | 12/1976 | Foster et al. | 585/850 X |
| 4,083,887 | 4/1978 | Foster et al. | 585/855 X |
| 4,150,063 | 4/1979 | Besozzi et al. | 585/855 X |
| 4,491,516 | 1/1985 | Polleck et al. | 208/248 |

FOREIGN PATENT DOCUMENTS

| | | | |
|---|---|---|---|
| 809584 | 4/1969 | Canada | 423/244 R |
| 2304963 | 2/1972 | Fed. Rep. of Germany | 585/855 |
| 1142339 | 2/1969 | United Kingdom | 208/244 |

OTHER PUBLICATIONS

Harshaw Catalyst Technical Bulletin No. 781.

*Primary Examiner*—Glenn Caldarola
*Attorney, Agent, or Firm*—Mark A. Montgomery; John K. Abokhair; M. Norwood Cheairs

[57] ABSTRACT

The present invention relates to a process for removing carbonyl sulfide from a liquid hydrocarbon feedstock, said process comprising the steps of (a) passing said hydrocarbon feedstock over an absorbent material comprising nickel deposited on a support material wherein nickel is present as both nickel oxide and metallic nickel and wherein the absorbent material has been conditioned by passing an inert gas flow containing a minor amount of propylene; and (b) recovering a liquid hydrocarbon stream having a substantially reduced carbonyl sulfide content.

16 Claims, No Drawings

PROCESS FOR REMOVING CARBONYL-SULFIDE FROM LIQUID HYDROCARBON FEEDSTOCKS

This is a continuation in part, of application Ser. No. 753,211, filed July 9, 1985 abandoned.

FIELD OF THE INVENTION

The present invention relates to a process for removing sulfur, present in the form of carbon oxysulfide or carbonyl sulfide, from liquid hydrocarbons. More particularly, the present invention relates to a process for the removal of carbonyl sulfide from hydrocarbon feedstocks containing propylene and to the conditioning of the absorbent material used in the process.

BACKGROUND OF THE INVENTION

Industrial applications of liquid hydrocarbons and particularly, liquified olefinic hydrocarbons, have become more increasingly specialized. The technology as presently developed utilizes highly efficient catalysts to convert these liquified hydrocarbon feedstocks into final product such as polymers. However, these highly efficient catalysts are very sensitive to contaminants, particularly sulfur contaminants, found in these hydrocarbon feedstocks.

In addition to the well known sulfur compounds such as hydrogen sulfide and mercaptans, the hydrocarbon feedstocks normally contain a small quantity of carbonyl sulfide (COS). Usually COS is present to the extent of only several hundred parts per million (ppm) by weight. However, even this small amount is normally beyond the allowable limits of an acceptable product. Since carbonyl sulfide is almost always formed when carbon, oxygen, and sulfur or their compounds, such as carbon monoxide, carbon disulfide and the like, are brought together at high temperatures, this compound is most frequently found in the hydrocarbon feedstocks resulting from thermal and/or catalytic cracking operations, although, in some cases, it has been found in virgin petroleum fractions.

To some extent, carbonyl sulfide is not as reactive as its companion in hydrocarbons, hydrogen sulfide. According to Kirk-Othmer's *Encyclopedia of Chemical Technology*, Vol. 13, pages 384-386, 1954 edition, carbonyl sulfide reacts slowly with the aqueous alkalimetal hydroxides and is only slowly hydrolyzed to carbon dioxide and hydrogen sulfide. This relatively unreactive characteristic of carbonyl sulfide makes it extremely difficult to remove from petroleum streams by conventional desulfurization techniques.

The presence of COS, even at very low concentrations, oftentimes renders olefins valueless for many purposes. For example, high purity olefins are required for the satisfactory production of many polymeric products, especially those useful as plastics, including polymers of ethylene, propylene, and the like. As a result, there has been a real need to improve techniques for removing COS from hydrocarbons, especially those used for polymer production.

Some of the known methods for removing carbon oxysulfide (COS) from hydrocarbon streams include the following. In British Patent Specification No. 1,142,339, published Feb. 5, 1969, the inventors teach a process for the removal of COS from gas mixtures in which unsaturated compounds such as propyne and propadiene are present, comprising passing said mixtures in liquid phase at atmospheric or superatmospheric pressures over a substance which contains one or more of the oxides of cadmium, zinc, nickel or cobalt supported on a carrier. It is stated that this process reduces the COS concentration to less than one (1) ppm.

U.S. Pat. No. 4,290,879 to Woodall et al, teaches the removal of carbonyl sulfide from propane and other similar liquified petroleum gas products by mixing liquid methanol with the untreated liquified gas and subsequently contacting the liquid mixture with solid potassium hydroxide. The COS concentration is reduced to less than one (1) ppm by volume.

U.S. Pat. No. 3,315,003 to Khelghatian, teaches that carbonyl sulfide can be effectively removed from normally gaseous hydrocarbons by first liquifying the hydrocarbons and then contacting them with soda-lime. The effluent gas must subsequently be dried to remove the moisture therefrom.

U.S. Pat. No. 3,284,531 to Shaw et al, teaches that COS can be removed by passing a fluid hydrocarbon through a bed of an anhydrous, weakly basic, anion exchange resin.

U.S. Pat. No. 3,282,831 to Hamm, discloses a method for removing COS from a hydrocarbon stream by utilizing an anionic exchange resin which is in the hydroxyl cycle and which is not fully hydrated.

The problems in purifying propylene and the like olefins are singularly complicated by the nearly identical boiling points of propylene and COS which makes COS removal by fractionation unsuitable. As a result, the levels of COS impurity in propylene stocks are often times intolerably high.

Still other disadvantages are encountered in the heretofore known procedures for the removal of COS from hydrocarbons, particularly those to be used for olefin polymerization. For example, some of the established methods introduce water or other contaminants into the hydrocarbon stream, all of which must be removed by additional processing in order to place the hydrocarbon in suitable condition for use. Any such additional processing, as well as any requirement to employ elevated temperatures adds materially and undesirably to the cost of the operation.

None of hhe above methods can reduce the COS content to less than fifty (50) parts per billion (ppb) by weight. Accordingly, it can be seen that there is a need for a process to reduce the COS concentration in a hydrocarbon stream to 50 ppb by weight or lower.

SUMMARY OF THE INVENTION

The present invention is directed to a process for the removal of carbonyl sulfide from hydrocarbon feedstocks, and more particularly from olefinic hydrocarbon feedstocks containing propylene and from about 1 to 10 ppm by weight of COS. In accordance with the present invention, COS is removed by passing the hydrocarbon feed over a conditioned absorbent material preferably comprising nickel deposited on a support material.

DETAILED DESCRIPTION OF THE PREFERRED EMBODIMENTS

The present invention relates to the removal of carbonyl sulfide (COS), sometimes referred to as carbon oxysulfide, from liquid hydrocarbon streams. Of particular interest is the treatment of liquid hydrocarbon streams containing olefins which streams are to be subsequently subjected to polymerization using polymerization catalysts. As stated previously, hydrocarbon streams containing propylene present a special problem for removal of COS by fractionation because of the nearly identical boiling points of propylene and COS. The present invention is, therefore, particularly useful for COS removal from hydrocarbon streams containing propylene.

The subsequent discussion will describe the invention in terms of treating liquid hydrocarbon feedstocks which essentially contain a major amount of propylene and minor amounts of propane and impurities such as COS. It should, however, be understood that the present invention is applicable to the treatment of liquid hydrocarbon streams in general and olefinic liquid hydrocabon streams in particular, i.e., hydrocarbon streams containing ethylene, propylene, butenes or any combination thereof since these olefins will react like propylene when contacted with the absorbent material.

It has been found that propylene absorbs onto the absorbent material when contacted with the hydrocarbon feedstocks containing propylene during the COS removal from said feedstocks and that the propylene absorption reaction is exothermic, occurring to a greater extent during start up. Under certain conditions, the temperature rise during propylene absorption may be very important, more particularly at the surface of the material of which the temperature may be much higher than that measured with a thermocouple, and it may thus damage the absorbent material. In addition the high temperatures cause undesired side-reactions, more particularly propylene dimerization and trimerization. The dimers are hexenes which copolymerize with propylene and break the regularity of the linear chain of isostatic propylene. As a result, the copolymer has a lower crystallinity than polypropylene, and thus a lower melting point; its mechanical resistance is also lower.

The Applicants have found that an excessive increase in the temperature of the absorbent material can be avoided by conditioning the material with a minor amount of the hydrocarbon to be treated. When the hydrocarbon feedstock contains propylene the conditioning comprises passing over the material an inert gas flow containing a minor amount of propylene.

The conditioning is conducted for a time at sufficient temperature and pressure under the inert gas flow, containing the minor amount of propylene, to condition the absorbent material without causing an excessive increase in temperature of said absorbent material.

The inert gas, used in the conditioning step is generally nitrogen. It is important that the inert gas does not contain oxygen, or contains the least possible amount of oxygen, preferably less than 10 ppm.

The propylene contained in the inert gas flow of the conditioning step can be pure propylene, but most often a minor amount of propylene in gaseous form is taken from the propylene feed that is to be treated to remove COS. This propylene feed is polymer grade propylene that contains the small amount of COS.

It is preferable to begin the conditioning procedure by passing essentially pure inert gas over the absorbent material, before introducing a minor amount of propylene in the inert gas flow. The propylene concentration in the inert gas flow preferably ranges from about 0.1 to 5 vol %, more preferably about 0.5 to 2 vol %, with about 1 vol % being most preferred.

The conditioning step is preferably carried out at about atmospheric pressure at or below ambient temperature preferably below about 15° C. The conditioning step is continued until the propylene concentration at the outlet equals that introduced indicating that the absorption reaction is complete. It is also possible to monitor the conditioning step by the passage of an exotherm, shown by thermocouples introduced within the absorbent material.

It is known that, when the absobbent material is prepared ex situ and stored under a non-oxidizing atmosphere (usually stabilized under $CO_2$), the traces of oxygen usually present therein have a negative effect on the properties of the absorbent material. This negative effect can be remedied if, before the above-mentioned conditioning step, the stored absorbent material is pretreated by passing a gaseous flow over said material, at a temperature between about 150° to 250° C.; preferably at about atmospheric pressure. The gaseous flow can be entirely inert, however, it is preferred that the gaseous flow at first be inert followed by a mixture of an inert gas and hydrogen wherein the hydrogen conentration is gradually increased from 1 to more than 95 vol %.

As above, the inert gas used in the pretreatment is generally nitrogen. In the pretreatment it is also important that the inert gas does not contain oxygen, or contain the least possible amount of oxygen, preferably less than 10 ppm.

In the pretreatment the inert gas flow is continued, prior to the introduction of hydrogen, until the concentration of the non-oxidizing gas at the outlet is sufficiently low. (e.g. lower than 0.1 vol %). When said non-oxidizing gas is carbon dioxide, two small exothermal endothermic temperature variations may be observed during the pretreatment. Each endotherm being associated with a rapid increase of $CO_2$ conentration in the vent gas. Hydrogen is then introduced, first at a concentration of about 1 vol % in the inert gas flow, then at concentrations gradually incresing to over 95 vol % while measuring the bed temperature which should not be allowed to rise above 300° C., preferably not above 250° C.

Following hydrogen pretreatment, the absorbent material is cooled under hydrogen flow to ambient temperature, purged free of hydrogen with an inert gas flow, then condition according to the above conditioning procedure.

The COS removal process of the present invention reduces the COS concentration in the treated hydrocarbon feedstock to 50 parts per billion by weight (ppb) or lower. The original COS concentration may be as high as 1000 parts per million by weight (ppm) or higher depending on the process of making and the origin of the hydrocarbon feedstock. Due to the expense and specialization of the present invention, it is preferrd to utilize other less costly and less complex processes to reduce the COS concentration to 70 ppm or less prior to treatment with the absorbent of the present invention.

While the subsequent discussion and examples may describe the absorbent material as a nickel absorbent material, the nickel absorbent material is only preferred and should not limit the reasonable scope of hhe present invention. It is envisioned that the pretreatment and conditioning of the present invention would be useful for treating any absorbent material that has an excessive increase in temperature; during COS removal, that could cause side-reactions and/or damage to the absorbent material.

The absorbent material of the present invention preferably comprises nickel deposited on a support material. Silica, silico-aluminas, alumina, kieselguhr and other similar materials can be ttilized as the support. When nickel is used the nickel is preferably present both as metallic nickel and as nickel oxide. The metallic nickel should constitute from about 35 to about 70 wt. % of the total nickel. Prefereably the absorbent comprises from about 40 to about 70 wt. % total nickel and from about 30 to about 60 wt. % support material.

The nickel can be deposited on the support by any of the several methods well known to those skilled in the art. For example, nickel can be deposited on the support by dissolving nickel nitrate in water, mixing the solution with the support and precipitating the nickel, for example in the form of nickel carbonate, and subsequently washing, drying and calcining the precipitate. The nickel deposited in this manner is then partially reduced by means of hydrogen to form metallic nickel in a quantity of from about 35 to about 70 wt % of the total quantity of nickel deposited, the remainder being in the form of nickel oxide.

In general, the size of the nickel crystallites after reduction is from about 10 to about 200 Å. The size of the nickel crystallites depends on the extent of reduction carried out. In fact, if the degree of reduction is increased, the size of the crystallites is increased but the absorbent material obtained does not have the desired properties. On the other hand, if the degree of reduction is too low, the crystallites still have good dimensions but the quantity of nickel available in this case is too small to ensure successfll purification of the feedstock.

The specific surface area of the absorbent material obtained after reduction is generally between 100 and 200 m$^2$/g.

The particle size of the absorbent material depends especially on the pressure loss allowed in the reactor; it has been noted, however, that it is advantageous to use the absorbent material in finely divided form. Preferably, the particle size of this material does not exceed about 3.5 mm and is most preferably from about 1 to about 2.5 mm.

In utilizing the latest generation of Ziegler-type catalysts in the production of polypropylene, it is essential that the propylene feedstock contain less than 50 ppb and preferably less than 30 ppb of COS. It has been unexpectedly found that by passing the propylene feedstock over an absorbent material conditioned according to the present invention and consisting essentially of from about 40 to about 70 wt. % nickel deposited on support materials selected from the group consisting of silica, silico-aluminas, alumina, kieselguhr and similar materials, wherein the nickel is present both as metallic nickel and as nickel oxide and wherein the metallic nickel represents from about 35 to about 70 wt. % of the total nickel, the feedstock obtained has a COS content not exceeding 30 ppb. This result is unexpected due to the degree of purity obtained and due to the fact that this process can be carried out either in the presence or absence of water.

In polypropylene production, the liquid hydrocarbon feedstock generally comprises more than 75 wt. % propylene, more particularly, from about 85 to about 99 wt. % propylene, and from about 1 to about 10 ppm COS. In one embodiment of the present invention, the liquid propylene feedstock is passed over the conditioned absorbent material at a temperature of from about 0° C. to about 90° C. and under sufficient pressure to keep the medium in the liquid phase. The liquid hourly space velocity (LHSV) utilized is from about 0.1 to about 20 and preferably from 0.2 to about 15.

The examples which follow are given in order to provide a better illustration of the process of the present invention, but without thereby restricting its scope.

EXAMPLE I a. Absorbent Material

An absorbent material was prepared in situ, comprising 43.3 wt. % of silica as support, on which nickel was deposited, wherein the nickel is present in the forms of 34 wt. % of NiO and of 22.7 wt. % of metallic nickel.

Before reduction, the absorbent material contained about 49 wt. % of nickel.

The absorbent material was finely divided so as to obtain particles of about 1 mm average dimension.

The specific area of said material was of 145 m$^2$/g.

b. Conditioning Step

A nitrogen flow was passed during 4 hours over the absorbent material, under atmospheric pressure, at a temperature of 20° C., and with a gaseous hourly space velocity (GHSV) of 125 1/1.h. During a further 12 hours, the conditioning was continued under the same conditions with nitrogen containing 1 vol % propylene.

c. Purification of the Feed

A liquid hydrocarbon feedstock containing 99 vol % of propylene, 1.5 ppm of COS and less than 5 ppm (detection limit) of hexenes, was passed on the conditioned absorbent material, at a temperature of 30° C., under a pressure of 1.5 MPa (15 bars) sufficient to maintain the feed in the liquid phase, and with a liquid hourly space velocity (LHSV) of 10 1/1.h.

After 5 hours, the purified feed contained 19 ppb of COS and less than 5 ppm (detection limit) of hexenes.

EXAMPLE II

An absorbent material was prepared according to the procedure described in Example I.a. It was stored under carbon dioxide during one month.

The absorbent material was pretreated by passing a gaseous flow thereon, at a temperature of 180° C. and under atmospheric pressure, said gaseous flow being formed first of nitrogen during 14 hours, then of a mixture of nitrogen and hydrogen during a further 24 hours, the hydrogen concentration therein being increased by about 5 vol % per hour up to more than 95 vol %. The absorbent material was cooled under said flow of nitrogen and hydrogen, then purged free of hydrogen with a nitrogen flow.

The absorbent material was conditioned as described in Example I.b., and the purification procedure of Example I.c. was repeated with the conditioned material. Results similar to Example I were obtained.

EXAMPLE III COMPARATIVE

Example I was repeated with the omission of the conditioning step I.b. After 5 hours, the purified feed contained 24 ppb of COS and 200 ppm of hexenes.

EXAMPLE IV COMPARATIVE

An absorbent material was prepared as described in Example I.a. and stored under carbon dioxide during one month.

A liquid hydrocarbon feedstock containing 99% of propylene, 2.7 ppm of COS and less than 5 ppm (detection limit) of hexenes, was passed on the absorbent material, at a temperature of 25° C., under a pressure of 1.5

MPa (15 bars) sufficient to keep the feed in the liquid phase, and with a LHSV of 5 l/l.h. After 5 hours, the purified feed contained 700 ppb of COS.

EXAMPLE V

A liquid hydrocarbon feedstock containing 99% of propylene and having a residual COS content of 2.7 ppm was passed over an absorbent material consisting of 43.3% by weight of silica as the support, on which nickel was deposited, the nickel being present in the form of NiO to the extent of 34% by weight and in the form of metallic Ni to the extent of 22.7% by weight.

Before reduction, the absorbent material contained about 49% by weight nickel.

The absorbent material was finely divided to give an average particle size of about 1 mm.

The specific surface area of this material was 145 m$^2$/g.

The above mentioned feedstock was thus passed over the absorbent material at ambient temperature, at a sufficient pressure to keep the feedstock in the liquid phase (15 bars), and at an LHSV of 5 l/l.h.

The purified feedstock had a COS content of 18 ppb.

EAMPLE VI

A liquid hydrocarbon feedstock containing 99 wt. % propylene and having different residual COS content was passed over the same absorbent material as in Example V.

The nickel containing absorbent material had a nickel content of about 49% by weight. The absorbent material was finely divided so as to give an average particle size of about 1 mm. The specific area of this material was about 145 m$^2$/g.

The feedstock was passed over said nickel containing material under various operating conditions, which are indicated in Table I.

As can be seen from the results, the purified feedstock had a COS content lower than 30 ppb, even when the feed contained water, which is known to be detrimental.

TABLE I

| LHSV | Temperature bed (°C.) | H$_2$O Content (ppm) | COS in ppm | COS out ppb |
|---|---|---|---|---|
| 4.95 | 20 | 13 | 1.8 | 22 |
| 5.05 | 25 | 8 | 4.5 | 20 |
| 4.8 | 23 | 8 | 3.1 | 18 |
| 9.3 | 16 | 14 | 1.85 | 15 |
| 15.05 | 15 | 14 | 1.3 | 24 |

EXAMPLE VII

A liquid hydrocarbon feedstock containing 95.6 wt. % propylene, 3.8 wt. % propane and 0.6 wt. % C$_4$, the water content of which being less than 10 ppm, and having different residual COS content was passed over the same absorbent as described in Examples V and VI except that the particles had an average diameter of 3.2 mm. This example is given to illustrate the activity of the catalyst over a long period of time.

The feedstock was passed under a pressure of 14 bar over a bed containing 2 liters of a nickel containing absorbent material.

The other operating conditions such as LHSV and temperature bed are indicated in Table II.

TABLE II

| Day | Temperature bed (°C.) | LHSV | COS in ppm | COS out ppb |
|---|---|---|---|---|
| 1 | 14 | 9.4 | 2.8 | 25 |
| 5 | 9 | 9.3 | 1.4 | 23 |
| 12 | 6 | 9.7 | 4.2 | 21 |
| 19 | 7 | 9.7 | 2.55 | 20 |
| 25 | 10 | 9.7 | 3.0 | 11 |
| 34 | 7 | 9.75 | 1.9 | 16 |
| 39 | 2 | 9.85 | 1.85 | 23 |
| 52 | 9 | 9.6 | 0.85 | 20 |
| 58 | 3 | 10.15 | 0.8 | 22 |
| 68 | 11 | 9.65 | 2.2 | 20 |
| 82 | 6 | 9.75 | 1.95 | 15 |
| 88 | 1 | 9.8 | 0.8 | 15 |

This example shows that even after 88 days the activity of the catalyst remained very high.

What is claimed is:

1. A process for removing carbonyl sulfide from a propylene containing liquid hydrocarbon, feedstock, said process comprising the steps of:
   (a) passing an inert gas flow containing propylene in a concentration in the range of about 0.1–5 volume % over an absorbent material thereby conditioning said absorbent materials so as to avoid an excess increase in temperature during hydrocarbon feedstock contacting;
   (b) passing said liquid hydrocarbon feedstock over the conditioned absorbent material of (a) to selectively absorb carbonyl sulfide thereon; and
   (c) recovering a liquid hydrocarbon stream having a substantially reduced carbonyl sulfide content.

2. The process according to claim 1, wherein the inert gas flow contains about 0.5 to 2 vol % propylene.

3. The process according to claim 2, wherein the inert gas flow contains about 1 vol % propylene.

4. The process according to claim 1, wherein essentially pure inert gas is passed over said absorbent material prior to the passing of said inert gas flow containing the minor amount of hydrocarbon.

5. The process according to claim 4, wherein the inert gas is nitrogen.

6. The process according to claim 1, wherein the absorbent material is pretreated prior to its conditioning by passing therethrough, at a temperature of about 150° to 250° C. and under atmospheric pressure, a gaseous flow comprising first an inert gas, then a mixture of inert gas and hydrogen containing an increasing hydrogen concentration.

7. A process for removing carbonyl sulfide from a liquid hydrocarbon feedstock, said process comprising the steps of:
   (a) passing an inert gas flow containing a minor amount of propylene over an absorbent material comprised of nickel deposited on a support material, wherein said nickel is present as both nickel oxide and metallic nickel, thereby conditioning said absorbent material so as to avoid an excess increase in temperature during hydrocarbon feedstock contacting;
   (b) passing a liquid hydrocarbon feedstock containing propylene over the conditioned absorbent material of (a) to selectively absorb carbonyl sulfide thereon; and
   (c) recovering a liquid hydrocarbon stream having a substantially reduced carbonyl sulfide content.

8. The process according to claim 7, wherein said inert gas flow contains about 0.1 to 5 vol % propylene and said liquid hydrocarbon feedstock comprises at least about 75% by weight of propylene.

9. The process according to claim 8, wherein said inert gas flow contains about 0.5 to 2 vol % propylene and said liquid hydrocarbon feedstock comprises at least about 95% by weight of propylene.

10. The process according to claim 9, wherein said inert gas flow contains about 1 vol % propylene.

11. The process according to claim 7, wherein (b step) is carried out at a temperature of about 0° C. to 90° C., at a sufficient pressure to retain said liquid hydrocarbon feedstock in liquid phase, and at an LSHV of about 0.1 to 20, and wherein the original concentration of the carbonyl sulfide in said liquid hydrocarbon feedstock is about 1 to 70 parts per million by weight.

12. The process according to claim 7, wherein said absorbent material has a particle size smaller than about 3.5 mm and a specific surface area of about 100 to 200 $m^2/g$, and comprises about 40 to 70 weight percent total nickel and the metallic nickel represents about 35 to 70 wt % of the total nickel with the balance being nickel oxide.

13. The process according to claim 12, wherein the support material is selected from the group consisting silica, silico-aluminas, alumina, kieselguhr, and combinations thereof.

14. A process for removing carbonyl sulfide from a liquid hydrocarbon feedstock, said process comprising the steps of:
  (a) passing a gaseous flow at a temperature of about 150° to 250° C. over an absorbent material comprised of nickel deposited on a support material wherein said nickel is present as both nickel oxide and metallic nickel, wherein said gaseous flow is first an inert gas, then a mixture inert gas and hydrogen thereby pretreating the absorbent material;
  (b) passing an inert gas flow containing a minor amount of propylene over the pretreated absorbent material of (a) thereby conditioning said absorbent material so as to avoid an excess increase in temperature during hydrocarbon feedstock contacting;
  (c) passing said liquid hydrocarbon feedstock over the conditioned absorbent material of (b) to effectively absorb carbonyl sulfide therein; and
  (d) recovering a liquid hyrdocarbon stream having a substantially reduced carbonyl sulfide content.

15. The process according to claim 14, wherein the hydrogen of said mixture in said gaseous flow is increased from about 1 to over 95 vol %, and step (a) is conducted at about atmospheric pressure.

16. The process according to claim 14, wherein said absorbent material has a particle size smaller than about 3.5 mm and a specific surface area of about 100 to 200 $m^2/g$, and comprises about 40 to 70 wt % total nickel wherein metallic nickel represent about 35 to 70 wt % of the total nickel, and wherein said hydrocarbon feedstock comprises at least about 75% by weight of propylene.

* * * * *